United States Patent [19]
Smith

[11] Patent Number: 5,919,947
[45] Date of Patent: Jul. 6, 1999

[54] TRACELESS SOLID PHASE SYNTHESIS OF INDOLE DERIVATIVES

[75] Inventor: Adrian Leonard Smith, Bishops Stortford, United Kingdom

[73] Assignee: Merck Sharp & Dohme Ltd., Hoddesdon, United Kingdom

[21] Appl. No.: 09/145,692

[22] Filed: Sep. 2, 1998

[30] Foreign Application Priority Data

Sep. 4, 1997 [GB] United Kingdom ............ 9718837

[51] Int. Cl.$^6$ .............. C07D 209/14; C07D 209/12; C07D 209/08
[52] U.S. Cl. ............ 548/469; 548/504; 548/509; 548/511; 548/506
[58] Field of Search ............................ 548/469, 504, 548/509, 511

[56] References Cited

PUBLICATIONS

Thompson, Lorin et al., Straightforward and General Methods for Coupling Alcohols to Solid Supports, Tetrahedron Letters, 35(50) pp. 9333–9336, Dec. 1994.

Fagnola, Maria et al., Solid–Phase Synthesis of Indoles Using the Palladium–Catalysed Coupling of Alkynes with Iodoaniline Derivatives, Tetrahedron Letters 38(13) pp. 2307–2310, Jun. 1997.

Zhang and Maryanoff, "Construction of Indole and Benzofuran Systems of the Solid Phase via Palladium–Mediated Cyclizations," *J. Org. Chem.* (1997), vol. 62, pp. 1804–1809.

Fagnola, et al., "Solid–Phase Synthesis of Indoles Using the Palladium–Catalysed Coupling of Alkynes with Iodoaniline Derivatives," *Tetrahedron Letters,* vol. 38, No. 13, (1997), pp. 2307–2310.

Thompson and Ellman, "Straightforward and General Method for Coupling Alcohols to Solid Supports," *Tetrahedron Letters,* vol. 35, No. 50, (1994), pp. 9333–9336.

Zhang, et al., "Synthesis of Trisubstituted Indoles on the Solid Phase via Palladium–Mediated Heteroannulation of Internal Alkynes," *Tetrahedron Letters,* vol. 38, No. 14, (1997), pp. 2439–2442.

*Primary Examiner*—Robert W. Ramjuer
*Assistant Examiner*—Dominic Keating
*Attorney, Agent, or Firm*—Philippe L. Durette; Melvin Winokur

[57] ABSTRACT

The present invention relates to a traceless solid phase process for the preparation of an indole derivative, which comprises the following steps:

(1) reaction of an optionally substituted 2-iodoaniline derivative via the nitrogen atom of the $NH_2$ moiety thereof with a dihydropyran-functionalized polymeric resin under conditions effective to form an aminal linkage;

(2) reaction of the tetrahydropyran aminal derivative thereby obtained with an acetylene derivative in the presence of a transition metal catalyst under conditions effective to promote indole formation;

(3) treatment of the product thereby obtained with acid, whereby the aminal linkage is cleaved and the desired indole derivative is liberated from the resin; and (4) isolation of the desired indole derivative thereby obtained.

3 Claims, No Drawings

TRACELESS SOLID PHASE SYNTHESIS OF INDOLE DERIVATIVES

The present invention relates to a process for preparing indole derivatives. More particularly, the invention concerns a traceless solid phase synthesis of 2,3-disubstituted and 2-unsubstituted-3-substituted indoles.

Several commercially available pharmaceutical agents are derivatives of indole. Examples include the antimigraine 5-HT$_{1B/1D}$ receptor agonists sumatriptan, naratriptan and zolmitriptan; and the antiemetic 5-HT$_3$ receptor antagonist tropisetron.

Various methods are known from the art for preparing compounds containing an indole nucleus. Perhaps the best known of these is the so-called Fischer indole synthesis, whereby a suitable phenylhydrazine derivative is reacted with the appropriate aldehyde or ketone, usually under acidic conditions. Larock and Yum, in *J. Am. Chem. Soc.*, 1991, 113, 6689–6690, describe a palladium-catalysed reaction between an o-iodoaniline and a substituted acetylene derivative to form the indole ring system.

Taking advantage of the Larock procedure, a highly efficient synthesis of the antimigraine clinical development candidate rizatriptan (MK-0462), and structurally related analogues thereof, is described in WO 95/32197.

Several reports have appeared recently describing solid phase synthetic approaches to indoles (see, for example, Zhang & Maryanoff, *J. Org. Chem.*, 1997, 62, 1804–1809; Zhang et al., *Tetrahedron Lett.*, 1997, 38, 2439–2442; and Fagnola et al., *Tetrahedron Lett.*, 1997, 38, 2307–2310). However, all these methods rely on resin-tethering substituents such as amines and carboxylic acids which appear in some form as extraneous polar substituents in the final molecules when cleaved from the resin. This approach limits the usefulness of the resulting solid phase chemistry to the practitioner interested in investigating structure-activity relationships where these extraneous polar tethering substituents are not wanted. In an area such as neuroscience, where the drug molecule is required to penetrate across the so-called "blood-brain barrier", polar substituents within the molecule are very often detrimental. Strategies which avoid the need for extraneous polar tethering substituents—the so-called "traceless" approach—are accordingly of benefit in such circumstances.

The reaction described in the Larock publication referred to above, and also in WO 95/32197, takes place in the solution phase. There is no disclosure or suggestion in either of these publications, nor indeed in any of the prior art available to date, that such a reaction can be adapted for use in a traceless solid phase synthesis of substituted indoles. However, we have now found an adaptation of the Larock procedure which is amenable to the preparation of substituted indoles under traceless solid phase conditions.

The present invention provides a process for the preparation of an indole derivative, which comprises the following steps:

(1) reaction of an optionally substituted 2-iodoaniline derivative via the nitrogen atom of the NH$_2$ moiety thereof with a dihydropyran-functionalized polymeric resin under conditions effective to form an aminal linkage;

(2) reaction of the tetrahydropyran aminal derivative thereby obtained with an acetylene derivative in the presence of a transition metal catalyst under conditions effective to promote indole formation;

(3) treatment of the product thereby obtained with acid, whereby the aminal linkage is cleaved and the desired indole derivative is liberated from the resin; and (4) isolation of the desired indole derivative thereby obtained.

The 2-iodoaniline derivative employed in step (1) of the process according to the invention may be unsubstituted, or substituted by one or more substituents. Suitably, the 2-iodoaniline derivative is unsubstituted, or substituted by one or two substituents. In one embodiment, the 2-iodoaniline derivative is unsubstituted. In another embodiment, the 2-iodoaniline derivative is monosubstituted.

A suitable dihydropyran-functionalized polymeric resin for use in step (1) of the process according to the invention comprises the (methylpolystyrene-1%-divinylbenzene)-derived resin described by Thompson and Ellman in *Tetrahedron Lett.*, 1994, 35, 9333–9336, which is prepared by treating Merrifield resin with the sodium salt of 6-hydroxymethyl-3,4-dihydro-2H-pyran in dry N,N-dimethylacetamide followed by rinsing and drying. Where this resin is employed in step (1) above, the reaction is conveniently carried out under acidic conditions, advantageously by utilizing a 3:1 molar ratio of the 2-iodoaniline derivative to resin in the presence of camphorsulfonic acid or pyridinium p-toluenesulfonate. Typically, the reaction will be effected at an elevated temperature, e.g. a temperature in the region of 70° C., in an inert solvent, e.g. a halogenated hydrocarbon solvent such as 1,2-dichloroethane.

The acetylene derivative employed in step (2) of the process according to the invention will generally possess the requisite substituents which it is desired to be present in the indole derivative obtained at the end of the reaction sequence, or precursors to such substituents. In particular, where the desired indole product is unsubstituted at the 2-position, the acetylene derivative employed in step (2) will suitably possess a silyl substituent, e.g. trimethylsilyl (TMS) or triethylsilyl (TES), which will be removed after formation of the indole nucleus by protodesilylation under the acidic conditions of step (3) as described above.

The transition metal catalyst employed in step (2) of the process according to the invention is suitably a palladium-containing catalyst. Typical catalysts include palladium(II) acetate, optionally in the presence of triphenylphosphine, and dichlorobis(triphenylphosphine)palladium(II). A preferred catalyst is dichlorobis(triphenylphosphine)palladium(II).

The transition metal catalysed indole formation reaction described in step (2) above is advantageously carried out under basic conditions. Typical basic reagents of use in the reaction include sodium carbonate, potassium carbonate, sodium acetate or potassium acetate, optionally in the presence of lithium chloride or tetra-n-butylammonium chloride; and tetramethylguanidine. A preferred base is tetramethylguanidine. The reaction is conveniently effected in a polar aprotic organic solvent such as N,N-dimethylformamide, typically at an elevated temperature, e.g. a temperature in the region of 80–110° C. A particularly advantageous technique is found to be double coupling, which comprises heating the reactants for approximately 5 hours, draining, replenishing with fresh reagents, and heating again for approximately 16 hours.

Cleavage of the aminal linkage and liberation of the desired indole derivative from the resin, as described in step (3) of the process according to the invention, takes place under acidic conditions. A suitable reagent for effecting this transformation is 10% trifluoroacetic acid, typically in a halogenated hydrocarbon solvent such as dichloromethane. As alluded to above, where the product obtained from step (2) possesses a silyl moiety in the 2-position, this moiety will generally be removed by protodesilyation under the acidic conditions of step (3), and the product obtained at the end of the reaction sequence will accordingly be a 2-unsubstituted-3substituted indole.

Once the desired indole derivative has been liberated from the resin by cleavage of the aminal linkage, it can then be isolated, as described in step (4) of the process according to the invention. Typically, the isolation procedure will comprise filtration of the reaction mixture, if necessary, followed by removal of solvent to afford a substantially pure sample of the desired indole derivative.

The traceless solid phase process according to the present invention possesses several advantages as compared with previously known indole synthesis procedures. For example, following a judicious choice of reactants and reaction conditions, the procedure is highly efficient, affording good yields of product with excellent regioselectivity. Once liberated from the resin, the desired indole product is very readily obtained, requiring the minimum of post-cleavage workup, and often simply removal of solvent. Furthermore, the overall process is readily amenable to automated high-speed parallel synthesis, making it adaptable as the basis of a split-mix combinatorial strategy and hence ideally suited to carrying out structure-activity investigations in the context of a drug-discovery programme.

In an illustrative embodiment, the present invention provides a process for the preparation of an indole derivative of formula I:

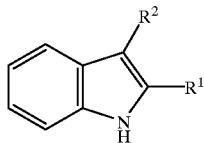

(I)

wherein $R^1$ represents hydrogen, $C_{1-6}$ alkyl or phenyl;

$R^2$ represents $C_{1-6}$ alkyl, phenyl, —$CH_2.CHR^3.OH$ or —$CH_2.CH_2.NR^4R^5$; and $R^3$, $R^4$ and $R^5$ independently represent hydrogen or methyl; which process comprises the following steps:

(A) reaction of the compound of formula II with a dihydropyran-functionalized polymeric resin of formula III:

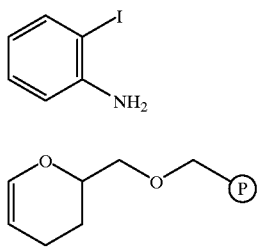

(II)

(III)

to obtain a compound of formula IV:

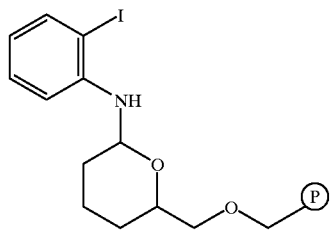

(IV)

(B) reaction of the tetrahydropyran aminal of formula IV thereby obtained with an acetylene derivative of formula V:

$$R^{11}\!-\!C\!\equiv\!C\!-\!R^2 \qquad (V)$$

wherein $R^2$ is as defined above, and $R^{11}$ represents $C_{1-6}$ alkyl, phenyl, or a silyl moiety of formula —$SiR^xR^yR^z$ in which $R^x$, $R^y$ and $R^z$ independently represent $C_{1-6}$ alkyl; in the presence of a transition metal catalyst; to obtain a compound of formula VI:

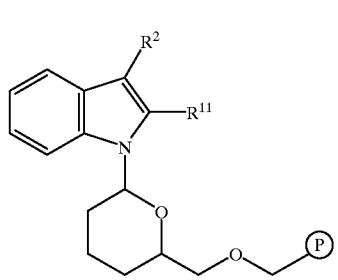

(VI)

wherein $R^2$ and $R^{11}$ are as defined above;

(C) treatment of the indole derivative of formula VI thereby obtained with acid, whereby the aminal linkage is cleaved and the indole derivative of formula I is liberated from the resin; and (D) isolation of the indole derivative of formula I as defined above thereby obtained.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl.

Where the compounds of formula I above have at least one asymmetric centre, they may accordingly exist as enantiomers. Where the compounds of formula I above possess two or more asymmetric centres, they may additionally exist as diastereoisomers. It is to be understood that the preparation of all such isomers and mixtures thereof in any proportion is encompassed within the scope of the present invention.

Particular values of $R^1$ include hydrogen, n-propyl, tert-butyl and phenyl.

Suitably, $R^3$ represents hydrogen.
Suitably, $R^4$ represents methyl.
Suitably, $R^5$ represents methyl.

When $R^2$ represents $C_{1-6}$ alkyl, suitable values include methyl, ethyl and n-propyl.

When $R^2$ represents —$CH_2.CH_2.NR^4R^5$, representative values include aminoethyl, N-methylaminoethyl and N,N-dimethylaminoethyl. A particular value is N,N-dimethylaminoethyl.

Suitably, $R^x$, $R^y$ and $R^z$ independently represent methyl, ethyl or tert-butyl. When $R^{11}$ represents a silyl moiety of formula —SiR$^x$R$^y$R$^z$, this is suitably a trimethylsilyl, triethylsilyl or tert-butyldimethylsilyl moiety, preferably trimethylsilyl.

Steps (A), (B), (C) and (D) of the above process correspond to steps (1), (2), (3) and (4) respectively of the process according to the invention described earlier. Accordingly, where a particular reactant, resin, catalyst or reaction condition is specified above for any of steps (1) to (4), it will be understood that such parameter will be equally applicable in the corresponding context for any of steps (A) to (D).

The following non-limiting Example is intended to illustrate the present invention.

EXAMPLE

1. Preparation of tetrahydropyran aminal linked resin

2-Iodoaniline (2.19 g, 10 mmol), pyridinium p-toluenesulfonate (500 mg) and dihydropyran-functionalized resin (prepared as described in *Tetrahedron Lett.*, 1994, 35, 9333) (5.0 g, 0.82 mmol/g) and 1,2-dichloroethane (50 ml) were mixed in a silanized round bottomed flask and heated at 70° C. for 16 h. The mixture was cooled and filtered into a polypropylene solid phase extraction cartridge, washing with CH$_2$Cl$_2$, 10% Hünig's base in DMF, DMF, CH$_2$Cl$_2$, MeOH and Et$_2$O. The tetrahydropyran aminal linked resin (IV) was dried in vacuo. Yield=5.899 g, loading=0.70 mmol/g (100%).

2. Solid phase indole synthesis 100 mg of the foregoing resin (0.70 mmol) was placed in a temperature-controlled solid phase reactor connected to a Schlenk line for inert atmosphere. The resin was washed with DMF (2×1 ml) and then treated with a prepared solution of Pd(PPh$_3$)$_2$Cl$_2$ (9.4 mg, 0.2 equiv.) and tetramethylguanidine (84 μl, 10 equiv.) in DMF (1 ml total volume) followed by the acetylene (V) (50 μl or 50 mg in 250 μl DMF). The mixture was heated with mechanical agitation at 110° C. for 5 h, drained, and then fresh reagents were added and heating continued for a further 16 h. The reactor was cooled, drained and washed with DMF, CH$_2$Cl$_2$, MeOH and Et$_2$O. The resin was air dried and then treated with 10% trifluoroacetic acid in CH$_2$Cl$_2$ (1 ml). The mixture was allowed to stand for 15 min. and then drained into a test tube. The cleavage was repeated for a further 15 min, and the resin was washed with CH$_2$Cl$_2$ (1 ml). The solvent was removed by SpeedVac to give pure desired indole of formula I.

Utilising the above procedure, the compounds of formula I in which R$^1$ and R$^2$ are specified in the Table below were prepared from the corresponding compounds of formula V in which R$^1$ and R$^2$ are also specified in the Table below:

| R$^{11}$ | R$^1$ | R$^2$ |
|---|---|---|
| Ph | Ph | Et |
| TMS | H | -CH$_2$CH$_2$OH |
| TMS | H | -CH$_2$CH$_2$NMe$_2$ |
| Ph | Ph | Ph |
| TMS | H | Ph |
| n-propyl | n-propyl | n-propyl |
| tert-butyl | tert-butyl | Me |

What is claimed is:

1. A process for the preparation of an indole group of formula I:

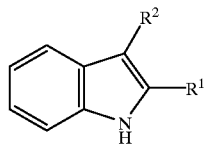

(I)

wherein

R$^1$ represents hydrogen, C$_{1-6}$ alkyl or phenyl;

R$^2$ represents C$_{1-6}$ alkyl, phenyl, —CH$_2$.CHR$^3$.OH or —CH$_2$.CH$_2$.NR$_4$R$_5$ and R$^3$, R$^4$ and R$^5$ independently represent hydrogen or methyl; which process comprises the following steps:

(A) reaction of the compound of formula II with a dihydropyran-functionalized polymeric resin of formula III:

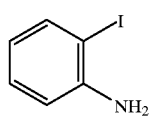

(II)

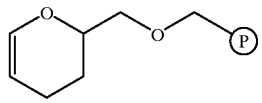

(III)

to obtain a compound of formula IV:

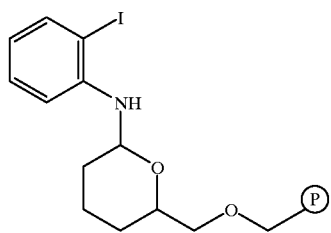

(IV)

(B) reaction of the tetrahydropyran aminal of formula IV thereby obtained with an acetylene group of formula V:

R$^{11}$—C≡C—R$^2$     (V)

wherein R$^2$ is as defined above, and R$^{11}$ represents C$_{1-6}$ alkyl, phenyl, or a silyl moiety of formula —SiR$^x$R$^y$R$^z$ in which R$^x$, R$^y$ and R$^z$ independently represent C$_{1-6}$ alkyl; in the presence of a transition metal catalyst; to obtain a compound of formula VI:

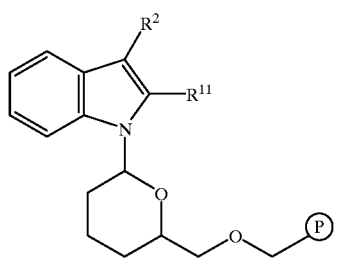

(VI)

wherein $R^2$ and $R^{11}$ are as defined above;

(C) treatment of the indole group of formula VI thereby obtained with acid, whereby the aminal linkage is cleaved and the indole group of formula I is liberated from the resin; and (D) isolation of the indole group of formula I as defined above thereby obtained.

2. A process as claimed in claim 1 wherein $R^1$ represents hydrogen, n-propyl, tert-butyl or phenyl.

3. A process as claimed in claim 1 wherein $R^2$ represents methyl, ethyl, n-propyl, phenyl, —$CH_2CH_2OH$ or —$CH_2CH_2NMe_2$.

* * * * *